US012746300B2

(12) United States Patent
Crane et al.

(10) Patent No.: US 12,746,300 B2
(45) Date of Patent: Sep. 29, 2026

(54) STERILISATION OF AN ANALYTE SENSOR COMPONENT

(71) Applicant: SciLogica Corp., Denver, CO (US)

(72) Inventors: Barry Colin Crane, Shenington (GB); Janet Lesley Walters, Oxfordshire (GB); Nicholas Paul Barwell, Warwickshire (GB); Praveen Sagar, Bucks (GB); Alasdair Allan Mackenzie, Herefordshire (GB)

(73) Assignee: SciLogica Corp., Denver, CO (US)

( * ) Notice: Subject to any disclaimer, the term of this patent is extended or adjusted under 35 U.S.C. 154(b) by 927 days.

(21) Appl. No.: 17/584,371

(22) Filed: Jan. 25, 2022

(65) Prior Publication Data

US 2023/0302180 A1 Sep. 28, 2023

(51) Int. Cl.
*A61L 2/18* (2026.01)
*A61B 5/145* (2006.01)
(Continued)

(52) U.S. Cl.
CPC ............ *A61L 2/24* (2013.01); *A61B 5/14532* (2013.01); *A61B 5/14546* (2013.01); *A61L 2/18* (2013.01);
(Continued)

(58) Field of Classification Search
CPC ..... A61L 2/16; A61L 2/18; A61L 2/20; A61L 2/202; A61L 2/204; A61L 2/206; A61L 2/208
See application file for complete search history.

(56) References Cited

U.S. PATENT DOCUMENTS 4,941,308 A * 7/1990 Grabenkort ......... A61M 25/002 53/445
6,009,339 A * 12/1999 Bentsen ............. A61B 5/14557 600/322

(Continued)

FOREIGN PATENT DOCUMENTS

EP 0847760 A2 6/1998
EP 2150279 A1 2/2010
WO WO-8602842 A1 * 5/1986 ............. A61L 2/206

OTHER PUBLICATIONS

Extended European Search Report regarding Application No. 22161673.3 dated Sep. 14, 2022.

(Continued)

*Primary Examiner* — Sean E Conley
*Assistant Examiner* — Eric Talbert
(74) *Attorney, Agent, or Firm* — Harness, Dickey & Pierce, P.L.C.

(57) ABSTRACT

A sensor component is sterilised for use in a system for measuring the concentration of one or more analytes in fluid in a fluid line. The sensor component comprises one or more sensing elements having an optical property that varies with the concentration of the one or more analytes in the fluid, and is configured to engage with the fluid line such that the sensing elements are exposed to the fluid. The method comprises introducing a gaseous sterilising agent into a sealed cavity via one or more ports providing fluid connection to the cavity, wherein the one or more sensing elements are exposed to the cavity, replacing the gaseous sterilising agent with a sterile liquid via the ports, and sealing the ports. Also disclosed is a sensor component with a configuration facilitating the application of the method.

22 Claims, 8 Drawing Sheets

(51) Int. Cl.
*A61L 2/20* (2026.01)
*A61L 2/24* (2006.01)
*A61L 103/00* (2026.01)
*B65B 55/02* (2006.01)
*B65B 55/18* (2006.01)

(52) U.S. Cl.
CPC ................ *A61L 2/20* (2013.01); *B65B 55/18* (2013.01); *A61B 2562/242* (2013.01); *A61L 2103/00* (2026.01); *A61L 2202/11* (2013.01); *A61L 2202/14* (2013.01); *B65B 55/025* (2013.01)

(56) References Cited

U.S. PATENT DOCUMENTS

| | | | | |
|---|---|---|---|---|
| 7,640,782 | B2 | 1/2010 | Hill | |
| 2004/0009542 | A1* | 1/2004 | Dumont .......... | A61M 1/362262 604/164.08 |
| 2004/0026341 | A1* | 2/2004 | Hogberg ................. | A61M 1/26 210/782 |
| 2005/0118056 | A1* | 6/2005 | Swanson .............. | A61B 5/1486 422/23 |
| 2006/0183985 | A1 | 8/2006 | Brister et al. | |
| 2007/0084144 | A1* | 4/2007 | Labrecque ............. | A61B 50/30 422/26 |
| 2008/0264140 | A1 | 10/2008 | Hill | |
| 2011/0004124 | A1* | 1/2011 | Lessar .................. | A61N 1/3758 600/587 |
| 2015/0282751 | A1* | 10/2015 | Konno ................. | A61B 5/1495 600/365 |
| 2016/0114975 | A1* | 4/2016 | Butler ..................... | B65F 1/141 53/551 |
| 2019/0241926 | A1* | 8/2019 | McKinlay .......... | A61B 5/14532 |
| 2020/0030515 | A1* | 1/2020 | Merchant ........... | A61B 5/02427 |
| 2020/0046951 | A1* | 2/2020 | Hoshino .............. | A61B 5/6847 |
| 2020/0166450 | A1* | 5/2020 | Riechers ................ | G01N 21/77 |
| 2021/0045666 | A1* | 2/2021 | Simpson ............ | A61B 5/14735 |
| 2021/0255103 | A1 | 8/2021 | Mackenzie et al. | |

OTHER PUBLICATIONS

Crane et al, The Development of a Continuous Intravascular Glucose Monitoring Sensor. J. Diabetes Sci Technol, 2015,1-11.

* cited by examiner

STERILISATION OF AN ANALYTE SENSOR COMPONENT

FIELD

The present invention relates to methods of sterilising sensor components used in systems for measuring the concentration of analytes in a fluid, in particular for sensor components that determine the concentration of analytes by changes in the optical property of one or more sensing elements.

BACKGROUND

It is desirable in many areas to be able to determine the concentration of an analyte in a fluid which may contain a mixture of several different substances. For example, in clinical settings it is important to be able to accurately determine the concentration of oxygen in a patient's blood in real time to detect and prevent hypoxia. Examples of clinical settings where monitoring of blood analytes is important include cardiopulmonary bypass (CPB), extracorporeal membrane oxygenation (ECMO), and continuous renal replacement therapies (CRRT). Continuous monitoring provides continuous patient status information to the clinician that will aid in therapy, eliminating blind intervals and reducing the risk to the patient.

For the types of sensor component considered herein, changes in analyte concentration are detected through changes in the optical property of one or more sensing elements. These are ideal for continuous monitoring, because they can be designed to have low levels of drift in their optical properties over time due to factors other than the analyte concentration. This means they can provide regular, accurate measurements over extended periods of time while reducing the need to take regular blood samples or perform frequent and time-consuming calibration procedures.

SUMMARY

In order to measure the concentrations of analytes in the fluid, it is necessary for parts of the sensor component to come into contact with the fluid. However, at least some of the sensing elements and other materials used in this type of sensor component become hydrated in use when exposed to the fluid. If the sensor component is supplied with the sensing elements in a non-hydrated state, it can take several hours for the optical properties of the sensing element to stabilize following exposure to the fluid. This is impractical in real-world contexts, and so the sensor components must be supplied with the sensing elements already in a hydrated state.

In addition, particularly in clinical contexts, it is important that the sensor components are supplied to the end user in a sterile condition. Because the sensor component must come into contact with the fluid in use, sterilisation reduces the risk of contamination of, for example, a patient's blood by foreign biological matter that could be introduced to the sensor component during manufacture.

A challenge is therefore to supply the sensor component to the user in a sealed, sterile package, while simultaneously keeping the sensing elements in a hydrated state, potentially for extended periods of time during the shelf life of the sensor component.

At present, this is achieved by sealing the sensor component in packaging with a hydrating fluid, and then sterilising the entire sealed package using gamma irradiation with the sensor component in a wet condition. However, ionising radiation generates highly reactive free radicals and reactive oxygen species which can be deleterious to the sensing elements and connector materials. This can cause drift in the optical properties of the sensor component and loss of signal when the sensor component is used.

Sterilisation with a gaseous sterilising agent, such as ethylene oxide, is a much more benign method of sterilisation. However, this must be carried out dry to prevent the gaseous sterilising agent interacting with the fluid, which can create or deposit chemicals inside the sensor component that are themselves damaging to the sensing elements and materials of the sensor component, or which create a risk of contamination of the sensor component that would potentially cause harm to a patient.

It is therefore desirable to provide a method of sterilisation that reduces damage to the sensor component, and which allows the sensor component to be supplied in a sterile, hydrated state.

According to a first aspect of the invention, there is provided a method of sterilising a sensor component for use in a system for measuring the concentration of one or more analytes in fluid in a fluid line, the sensor component comprising one or more sensing elements having an optical property that varies with the concentration of the one or more analytes in the fluid, the sensor component being configured to engage with the fluid line such that the sensing elements are exposed to the fluid in the fluid line, and a connector configured to connect to one or more optical waveguides, the sensor component being configured to transmit light between the one or more optical waveguides and the one or more sensing elements, the method comprising introducing a gaseous sterilising agent into a sealed cavity via one or more ports providing fluid connection to the cavity, wherein the one or more sensing elements are exposed to the cavity, replacing the gaseous sterilising agent with a sterile liquid via the ports, and sealing the ports.

By exposing the sensing elements to a cavity, the environment of the sensing elements can be controlled and kept sterile as the gaseous sterilising agent is replaced by the sterile liquid. In addition, the cavity full of sterile liquid is sealed using the ports, ensuring that the sensing elements remain exposed to the sterile liquid and in a hydrated state until the sensor component is used. This method thereby enables the use of more benign gaseous sterilising agents, improving the accuracy of subsequent measurements using the sensor component.

In some embodiments, the step of introducing a gaseous sterilising agent into the cavity comprises placing the sensor component into a sealed environment and introducing the gaseous sterilising agent into the sealed environment, the step of replacing the gaseous sterilising agent being carried out without removing the sensor component from the sealed environment. The use of a sealed environment, for example a sterilisation bag, means that the exterior surfaces of the sensor component can also be kept sterile during the procedure, thereby further reducing the chance of contamination of the surfaces of the sensor component that will come into contact with the fluid in use.

In some embodiments, the gaseous sterilising agent remains in the cavity for at least 1 hour before carrying out the step of replacing the gaseous sterilising agent. This allows sufficient time to ensure the relevant parts of the sensor component are completely sterilised.

In some embodiments, the method further comprises preconditioning the sensor component prior to introducing the gaseous sterilising agent by exposing the sensor component to a predetermined temperature and/or humidity for a predetermined length of time. This can ensure optimal conditions for the sterilisation using the gaseous sterilising agent to be most effective.

In some embodiments, replacing the gaseous sterilising agent with a sterile liquid via the ports comprises replacing the gaseous sterilising agent with a sterile gas via the ports, and subsequently introducing the sterile liquid via the ports. This reduces the likelihood of any of the gaseous sterilising agent remaining in the cavity and coming into contact with the sterile liquid.

In an embodiment, replacing the gaseous sterilising agent with a sterile gas via the ports comprises removing the gaseous sterilising agent by evacuation via the ports, and subsequently introducing the sterile gas via the ports. Evacuation further improves the removal of the gaseous sterilising agent to prevent any gaseous sterilising agent remaining in the cavity after sterilisation.

In some embodiments, the method is carried out at a temperature in a range from 35° C. to 65° C. This provides optimal conditions for the gaseous sterilising agent to be most effective.

In some embodiments, the gaseous sterilising agent is one of ethylene oxide, ozone, hydrogen peroxide, nitrogen dioxide, and formaldehyde. These gaseous sterilising agents are readily available and suitable for sterilising devices used in clinical contexts.

In some embodiments, the sterile liquid is a calibration solution containing predetermined concentrations of the one or more analytes. This facilitates calibration of the sensor component at the point of use.

In some embodiments, the one or more ports comprise two ports, and the steps of introducing the gaseous sterilising agent and replacing the gaseous sterilising agent are carried by flowing the gaseous sterilising agent and sterile liquid between the two ports. Using a flow of gas and liquid between two ports can ensure that the fluids more effectively penetrate all parts of the cavity.

In some embodiment sealing the ports comprises permanently sealing the ports. This reduces the chance of later contamination of the cavity in embodiments where the ports are used only during the calibration procedure.

In some embodiments, sealing the ports comprises sealing the ports with removable elements. This can reduce the chance of contamination of the cavity where the ports may need to be used again at a later time following sterilisation.

In some embodiments, the method further comprises, prior to the step of introducing a gaseous sterilising agent into the cavity, connecting tubing to the one or more ports, wherein the step of introducing the gaseous sterilising agent comprises flowing the gaseous sterilising agent through the tubing, the step of replacing the gaseous sterilising agent comprises flowing the sterile liquid through the tubing, and the step of sealing the one or more ports comprises sealing the tubing, and cutting the tubing outside the position where the tubing is sealed such that a sealed section of the tubing remains connected to the ports. Using tubing can provide additional flexibility in placing and connecting the necessary parts during sterilisation, and also provides a convenient way to seal the ports.

In some embodiments, the tubing comprises a tubing valve configured to open and close the tubing, the step of introducing the gaseous sterilising agent is performed with the tubing valve open, the step of replacing the gaseous sterilising agent is performed with the tubing valve open, the tubing is cut between the position where the tubing is sealed and the tubing valve, and the method further comprises closing the tubing valve prior to the step of sealing the ports. Inclusion of a tubing valve makes it easier for the user to control the flow of fluids through the tubing during the sterilisation procedure.

In some embodiments, the tubing is sealed using ultrasonic welding or solvent sealing. These are convenient methods for sealing tubes, which may typically be formed of plastic.

In some embodiments, the sensor component further comprises a component valve in respect of the or each port configured to open and close the port the step of introducing the gaseous sterilising agent is performed with the component valve open, the step of replacing the gaseous sterilising agent is performed with the component valve open, and the step of sealing the one or more ports comprises closing the component valve. Inclusion of a component valve allows the sensor component to be supplied with a valve permitting access to the cavity via the ports. This can be particularly advantageous if the sensor component is designed to be engaged with the fluid line in a shunt or bypass configuration.

In some embodiments, the sensor component defines the sealed cavity and comprises the one or more ports. This may be advantageous depending on the application of the sensor component.

In some embodiments, the sensor component is configured to engage with a wall of the fluid line. In some embodiments, the sensing elements are covered by a removable seal, the cavity being defined between the sensing elements and the removable seal. This is advantageous where the sensor component engages with the wall of the fluid line, because the removable seal can be removed immediately prior to engagement of the sensor component with the fluid line, thereby exposing the cavity and sensor elements to the fluid in the fluid line.

In some embodiments, the cavity is a conduit that is configured to be inserted into the fluid line for engagement of the sensor component with the fluid line. Inserting the cavity into the fluid line ensures the sensing elements are exposed to the fluid.

In some embodiments, the conduit is configured to be inserted into the fluid line in an in-line configuration. In-line configurations may be appropriate depending on the particular application of the sensor component and provide direct exposure to fluid in the main fluid line.

In some embodiments, the conduit is configured to be inserted into the fluid line in a shunt configuration. A shunt configuration may allow the sensor component to be changed without halting flow of fluid in the fluid line.

In some embodiments, a container defines the cavity and the sensor component is removably inserted into the cavity prior to introducing the gaseous sterilising agent. This may be advantageous depending on the type and configuration of the sensor component. The sensor component can then be removed from the cavity immediately prior to use.

According to a second aspect of the invention, there is provided a sensor component for use in a system for measuring the concentration of one or more analytes in fluid in a fluid line, the sensor component comprising one or more sensing elements having an optical property that varies with the concentration of the one or more analytes in the fluid, a connector configured to connect to one or more optical waveguides, the sensor component being configured to transmit light between the one or more optical waveguides and the one or more sensing elements, a removable seal covering the sensing elements, a sealed cavity between the sensing elements and the removable seal, the one or more sensing elements being exposed to the cavity, and one or more sealed ports in the cavity, wherein the sensor component is configured to engage with a wall of the fluid line following removal of the removable seal such that the sensing elements are exposed to the fluid in the fluid line.

A sensor component comprising a cavity with sealed ports and a removable seal on the cavity is particularly suited to use with embodiments of the method of sterilisation of the first aspect of the invention. The cavity enables the sensing elements to be kept exposed to a sterile liquid, and thereby keeping the sensing elements in a hydrated state, until immediately prior to use. The removable seal provides a quick and straightforward way to open the cavity to allow the sensing elements to be exposed to fluid in the fluid line.

In some embodiments, the sensor component comprises at least two sealed ports. This enables gas or liquid to be flowed through the cavity during sterilisation.

In some embodiments, the removable seal is configured such that the sensor component cannot engage with the wall of the fluid line prior to removal of the removable seal. This ensures the sensing elements will be properly exposed to fluid in the fluid line following engagement of the sensor component with the fluid line.

DRAWINGS

Embodiments of the present invention will now be described by way of non-limitative example with reference to the accompanying drawings, in which.

DETAILED DESCRIPTION

Figure 1:
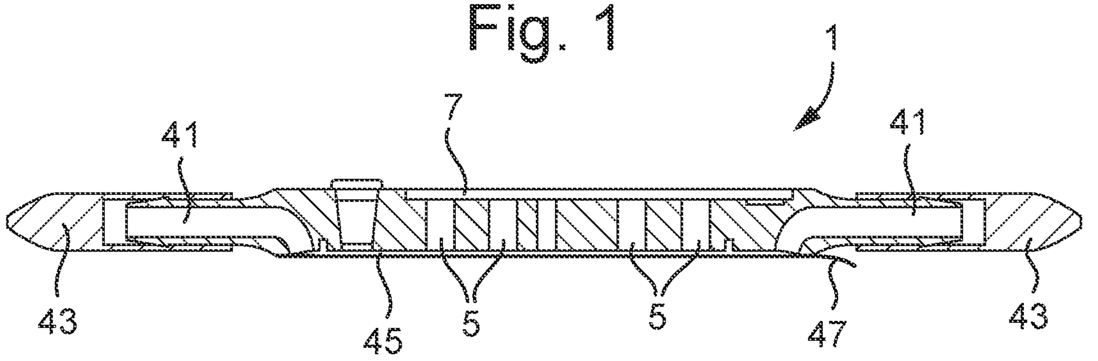
FIG. 1 is a cross-sectional view of a sensor component.
Figure 2:
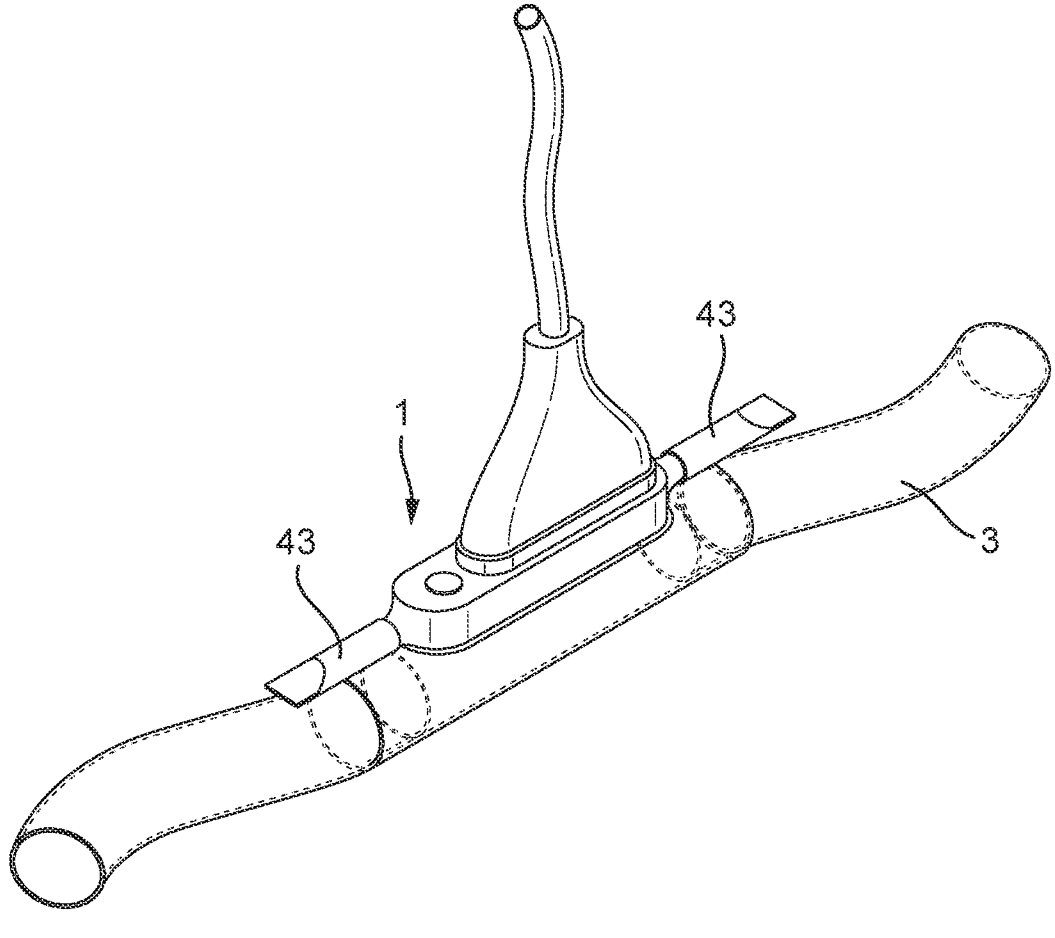
FIG. 2 is an isometric view of the sensor component engaged with a wall of a fluid line.

FIGS. 1 and 2 shows an example of a sensor component 1 with which the sterilisation methods described herein may be used. The sensor component 1 is for use in a system for measuring the concentration of one or more analytes in fluid in a fluid line 3. The system is preferably a system for use in clinical contexts, for example being part of ECMO, CPB, or CRRT machines as mentioned above. In such cases, the fluid in the fluid line 3 is blood of a patient. However, this is not essential, and the sensor component 1 may also be used in other contexts, for example monitoring of analyte concentrations in fluids other than blood. Analytes measured by the system using the sensor component 1 may include oxygen, carbon dioxide, hydrogen ions (i.e. pH), potassium, sodium, calcium, magnesium, ammonia, nitric oxide, or anaesthetic gases.

The sensor component 1 comprises one or more sensing elements 5. The sensor component 1 comprises four sensing elements, but this is not essential, and other embodiments may comprise one, two, three, or more than four sensing elements 5. The sensing elements 5 each comprise a luminescent compound, preferably a fluorescent compound, more preferably a fluorescent organic dye. The luminescent compound may be different for different sensing elements 5, and will depend on the analytes to be measured. Examples of suitable luminescent compounds include seminaphtharhodafluor (SNARF), mag-fluo-4, and derivatives thereof. The sensing element 5 may comprise the luminescent compound suspended in, dissolved in, or molecularly bonded to a matrix. The matrix may comprise a polymer, for example PMMA or polystyrene. Alternatively, the matrix may comprise a sol-gel or hydrogel.

The sensing element 5 has an optical property that varies with the concentration of the one or more analytes in the fluid. The optical property may be emission or absorption of light. In the case where the sensing element 5 comprises a luminescent compound, the optical property may be a luminescence lifetime. The optical property may be the same for all of the sensing elements 5, or may differ between sensing elements 5. Various measurement modalities may be used to minimize drift in sensors. Fluorescent lifetime and ratiometric modalities are commonly used when available, as these are less vulnerable to common sources of error that can cause drift. Ratiometric modalities take two measurements of light from the luminescent compound, for example at different wavelengths, and calculate a ratio. However, often straight intensity measurements methods are the only modalities available, and therefore it is important that aspects of the design of the sensor component 1 are chosen to minimize drift and inaccuracies.

The sensor component 1 is configured to engage with the fluid line 3 such that the sensing elements 5 are exposed to the fluid in the fluid line 3. As shown in FIG. 2, the sensor component 1 engages with the fluid line 3 with the sensing element 5 exposed to the interior of the fluid line 3 such that fluid flowing through the fluid line 3 past the sensor component 1 will come into contact with the parts of the sensor component 1 facing the interior of the fluid line 3.

The sensor component 1 comprises a connector 7 configured to connect to one or more optical waveguides. In the embodiments shown in FIGS. 1 to 3, the connector 7 comprises a recess in the sensor component 1. However, in general the connector 7 may take any suitable form, and may comprise retention elements such as clips or screws to prevent movement of the one or more optical waveguides relative to the connector 7.

The optical waveguides allow light to be transmitted to and from one or more light sources elsewhere in the system in which the sensor component 1 is used. Suitable light sources include LEDs or laser diodes. The optical waveguides may comprise optical fibres or optical fibre bundles to transmit the excitation light to the sensing elements 5. Light emitted from (or transmitted through) the sensing elements 5 is also returned via the optical waveguides to detectors in the system that detect the intensity of light from the sensing elements 5. In some embodiments, the sensor component 1 may comprise the one or more optical waveguides and/or the one or more light sources and detectors. The sensor component 1 is configured to transmit light between the one or more optical waveguides and the one or more sensing elements 5, such that the optical property of the sensing elements 5 can be measured.

Medical devices are typically terminally sterilized either by γ-irradiation, e-beam, or gaseous agents such as ethylene oxide. Both γ-irradiation and e-beam are ionizing radiations generating highly reactive free radicals via polymer degradation. This can cause ongoing plastic embrittlement of parts of the medical devices, leading to reduced lifespan. Free radical generation during irradiation also generates colour centres in the plastic and glass materials that are often used for optical components such as optical waveguides, hence causing a decrease in light transmission. This decrease in light transmission can be usually accommodated during calibration of the sensor component 1, unless light transmission is decreased to the point where the optical excitation used to measure the optical property of the sensing elements 5 is hindered. However, the transmission of the materials can be recovered by passing visible light through the optical components. This is exactly what happens during continuous monitoring, and leads to drift in the properties of the optical components during use (effectively causing a gradual, continuous change in the incident intensity of light into the sensing elements 5).

In addition, in the presence of small amounts of oxygen and water, peroxy and hydroxyl free radicals are generated during irradiation. These are extremely reactive, and are likely to react with the sensing elements 5, changing their optical property (for example by causing an effective change in the concentration of luminescent compound in the sensing element, or even the ability of the luminescent compound to luminesce by changing its quantum efficiency). In an attempt to minimize this, sensor components 1 may be γ-irradiated anhydrous and under nitrogen. However, this has the effect of stabilizing the organic free radicals, and when the sensor component is eventually introduced to oxygen and water (usually during use) then the peroxy and hydroxyl free radicals are generated again, leading to in-use drift in the properties of the sensing elements 5.

To avoid these disadvantages of sterilising sensor components 1 using irradiation, it is preferable to use more benign gaseous sterilising agents such as ethylene oxide. Gaseous sterilisation must typically be performed with the sensor component 1 in a dry state to avoid reaction of the gaseous sterilising agent with water. For example, if the sensor component 1 is wet with water, ethylene oxide will react with the water to form ethylene glycol.

However, the properties of the sensing elements 5 may change with the level of hydration. For example, the luminescent compound of the sensing elements 5 may be suspended in a hydrogel, which is up to 90% water. A change in the hydration can cause a change in the intensity of light reaching the luminescent compound, and an effective change in the concentration of the luminescent compound. Even hydrophobic components may take up water slowly. Therefore, the sensor component 1 has to be presented to the user with the sensing elements 5 in a fully hydrated state. This ensures stability of measurements and low hydration drift as soon as required by the user. Otherwise, if the hydration of the sensing elements 5 changes at the point of use, either in calibration or during continuous monitoring, the optical property of the sensing elements 5 will slowly change as the sensing elements 5 become hydrated. This results in significant drift, typically over a timescale of hours. To stabilize the hydration at the point of use would require the user to put the sensor component 1 through a stabilization phase that could last several hours before the sensor component 1 could be used. This would be impractical for use in real-world settings.

The method of sterilisation described herein addresses this conflict in the requirements to perform dry sterilisation, but still present the sensor component 1 sterile and in a hydrated state to minimise drift.

To facilitate this method, the sensor component 1 comprises a removable seal 47 covering the sensing elements 5, and a sealed cavity 45 is defined between the sensing elements 5 and the removable seal 47. The one or more sensing elements 5 are exposed to the cavity 45. The removable seal 47 in FIG. 1 is an aluminium foil layer with a tab, that is affixed by adhesive to the underside of the sensor component 1. However, this is not essential, and the removable seal 47 may in general be formed in any suitable manner, for example a removable plastic film or rigid cover.

Figure 3:
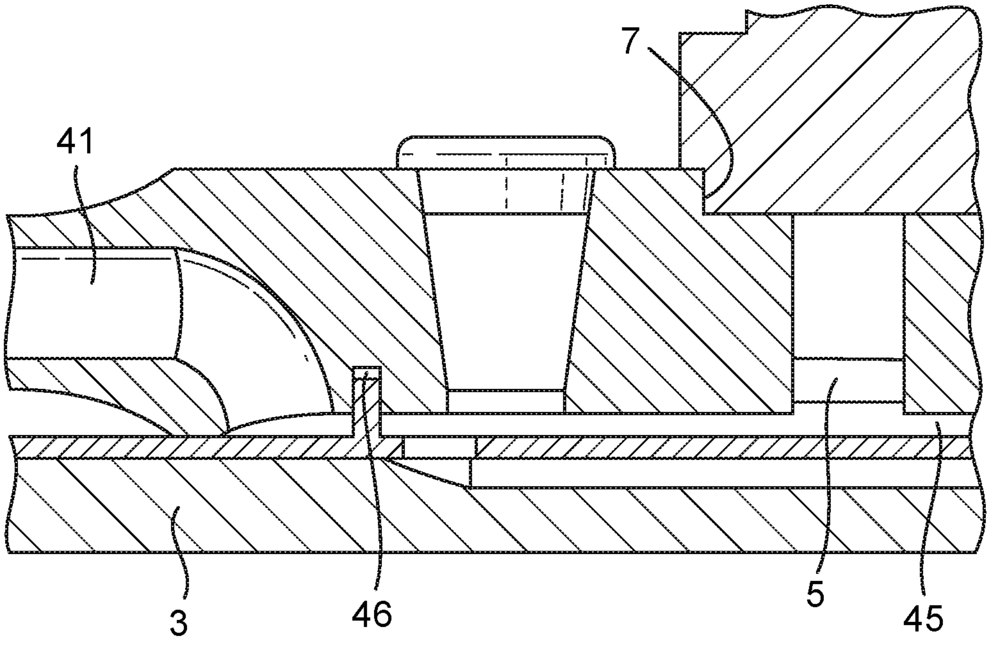
FIG. 3 is an enlarged view of a section of FIG. 1 showing the port and cavity.

The sensor component 1 of FIG. 1 is configured to engage with a wall of the fluid line 3. As shown in FIG. 3, the sensor component 1 is further configured to engage with a wall of the fluid line 3 following removal of the removable seal 47 such that the sensing elements 5 are exposed to the fluid in the fluid line 3. Once the removable seal 47 is removed, and the sensor component 1 engaged with the wall of the fluid line 1, the cavity 45 becomes a part of the interior of the fluid line 3, and will be filled with fluid from the fluid line 3 during use.

As shown in FIG. 3, the removable seal 47 is configured such that the sensor component 1 cannot engage with the wall of the fluid line 3 prior to removal of the removable seal 47. This prevents the user from engaging the sensor component 1 with the fluid line 3 without removing the removable seal 47, which would result in the sensing elements 5 not being exposed to fluid in the fluid line 3. In the example of FIG. 3, this is achieved using a recess 46 in the sensor component 1 which provides engagement with the wall of the fluid line 3, but is covered by the removable seal 47, however this is not essential, and any other suitable method may be used.

The sensor component 1 comprises two sealed ports 41 providing fluid connection to the cavity 45. The ports 41 are sealed when the sensor component 1 is provided to the end user, but may be unsealed to allow fluid connection to the cavity 45 from the exterior of the sensor component 1 during the sterilisation method. Two ports 41 is preferable, as they allow fluids such as the gaseous sterilising agent to be flowed in a continuous fashion from one port 41 to the other. However, it is not essential that the sensor component 1 comprise two ports 41, and in some embodiments, the sensor component 1 may comprise one port 41, or more than two ports 41.

Figure 4:
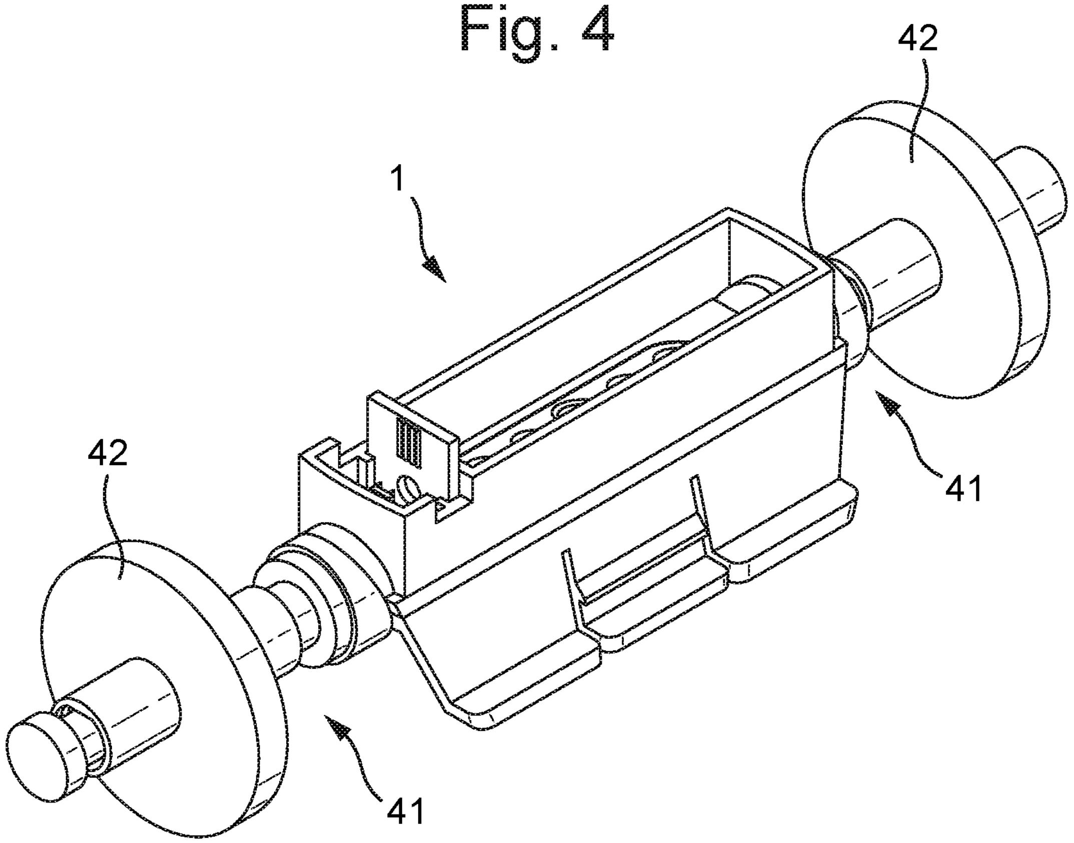
FIG. 4 shows an embodiment of the sensor component in which the ports comprise filters.

As shown in FIG. 4, in some embodiments, the ports 41 may comprise filters 42, for example to aid in keeping the connector sterile after sterilisation. The filters 42 may be configured to block bacteria passing through the filter 42. This can contribute to preventing bacteria from entering the component when the sterile liquid is used to replace the gaseous sterilising agent. For example, the filters 42 may be 0.22 micron filters. The filter 42 may be removable so that they can be removed from the component at an appropriate stage of connection to a fluid line at the point of use.

As will be discussed further below, it is not in general essential to the method that sensor components sterilised using the method define the sealed cavity 45 and comprise the one or more ports 41. However, the sensor component 1 shown in FIGS. 1 to 3 is particularly suited to the present method.

Figure 5:
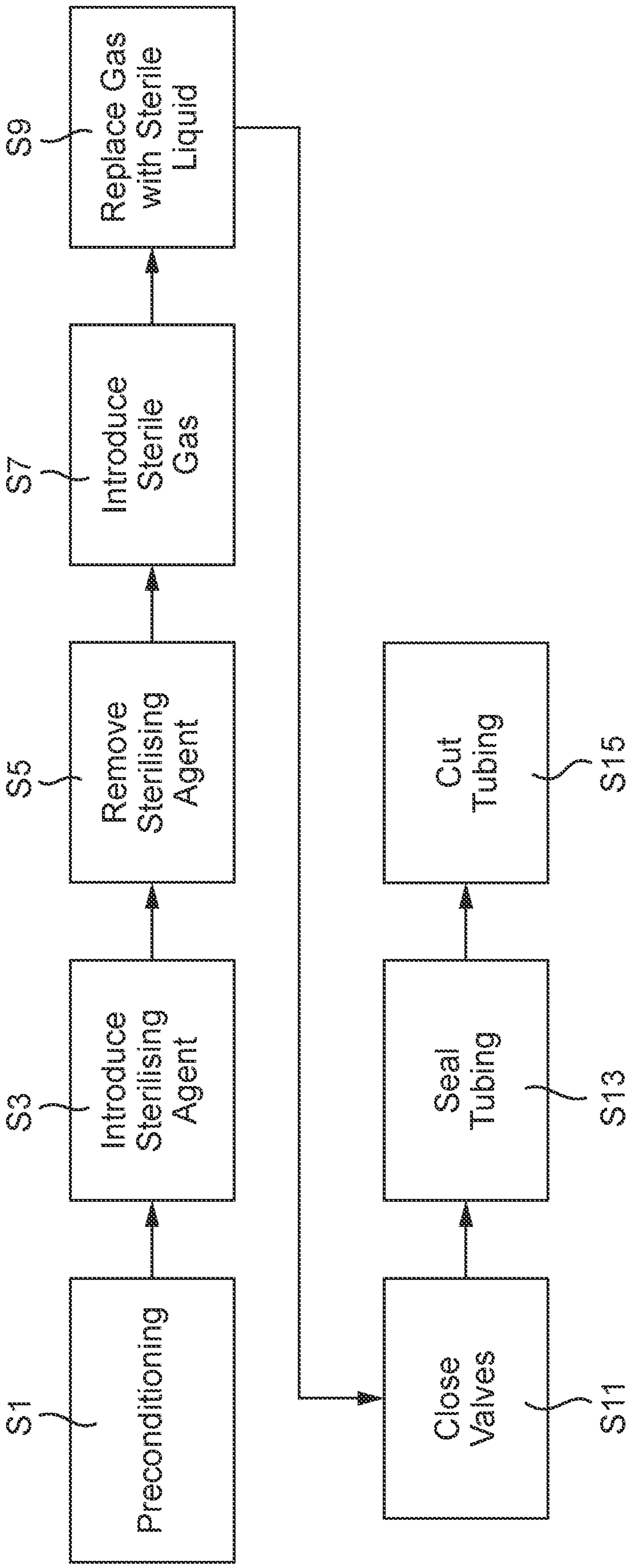
FIG. 5 is a flowchart of an embodiment of the method of sterilisation

A method of sterilising a sensor component 1 for use in a system for measuring the concentration of one or more analytes in fluid in a fluid line is shown in FIG. 5. This method allows for sterilisation with a gaseous sterilising agent, while also allowing the sensor component 1 to be delivered in a sterile, hydrated state to the end user.

The method comprises preconditioning S1 the sensor component 1 prior to introducing the gaseous sterilising agent by exposing the sensor component 1 to a predetermined temperature and/or humidity for a predetermined length of time. The predetermined length of time may be at least 4 hours, optionally at least 8 hours, optionally at least 1 day, optionally at least 2 days-1. Pre-conditioning S1 the sensor component 1 by pre-humidification and/or pre-heating places the sensor component 1 in a condition where the gaseous sterilising agent will have optimal effect and be most effective in sterilising the sensor component 1. The preconditioning S1 is preferred, but not essential and may be omitted in some embodiments, depending for example on the choice of gaseous sterilising agent. Preferably, the method is carried out at a temperature in a range from 35° C. to 65° C. Where preconditioning S1 comprises exposing the sensor component 1 to a predetermined temperature, the predetermined temperature may be in the range from 35° C. to 65° C.

The method further comprises introducing S3 a gaseous sterilising agent into a sealed cavity 45 via one or more ports 41 providing fluid connection to the cavity 45, wherein the one or more sensing elements 5 are exposed to the cavity 45. The gaseous sterilising agent is preferably one of ethylene oxide, ozone, hydrogen peroxide, nitrogen dioxide, and formaldehyde. Most preferably, the gaseous sterilising agent is ethylene oxide.

As discussed above in relation to the sensor component of FIGS. 1 to 3, the cavity may be defined by the sensor component 1, and the sensor component 1 may comprise the one or more ports 41. In particular, the sensing elements 5 may be covered by a removable seal 47, the cavity 45 being defined between the sensing elements 5 and the removable seal 47. In this case, the method is carried out with the removable seal 47 in place. However, it is not essential that the cavity be defined by the sensor component, or that the sensor component comprise the ports 41, as will be discussed further below.

Figure 6:
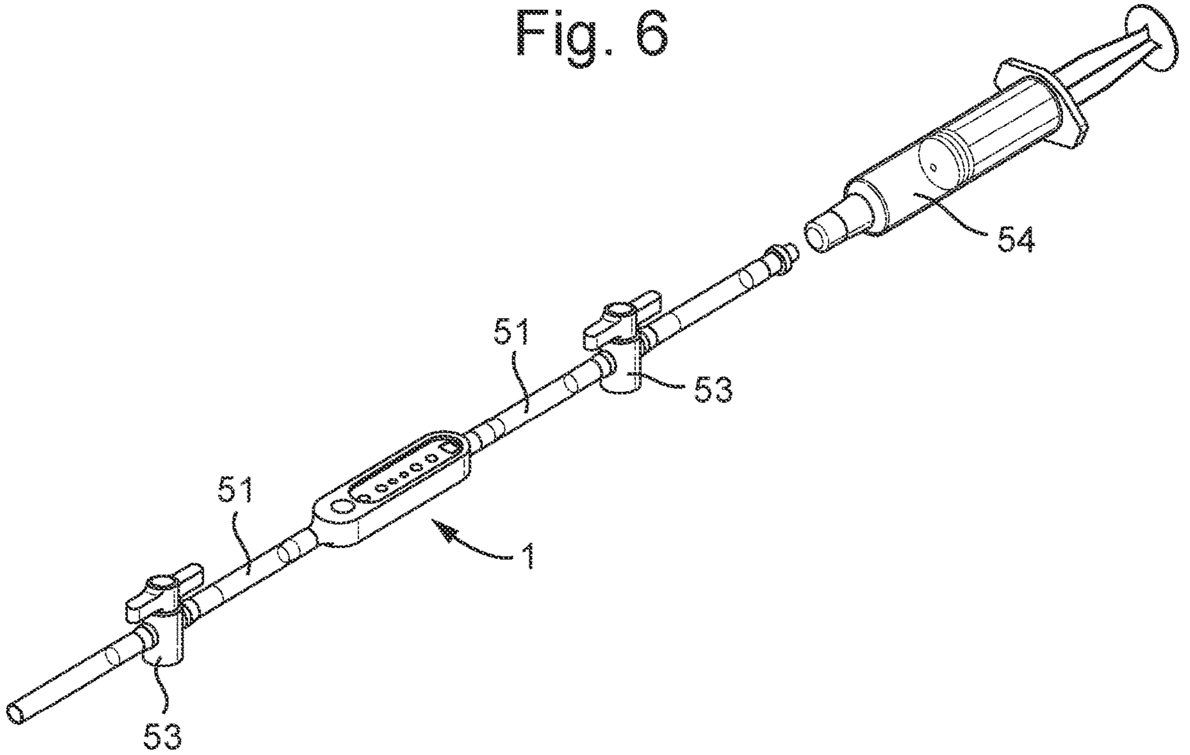
FIG. 6 shows a sensor component during introduction of the gaseous sterilising agent.

FIG. 6 illustrates the step S3 of introducing a gaseous sterilising agent. In this embodiment, prior to the step S3 of introducing a gaseous sterilising agent into the cavity 45, tubing 51 is connected to the ports 41. The tubing 51 comprises a tubing valve 53 configured to open and close the tubing 51. The tubing 51 and tubing valve 53 allow better control of the flow of gaseous sterilising agent into and out of the cavity 45 during the sterilisation method, but are not essential and may be omitted in some embodiments of the method.

The sensor component 1 comprises two ports 41, and introducing S3 the gaseous sterilising agent comprises flowing the gaseous sterilising agent between the two ports 41. This is in general not necessary, and in embodiments with only a single port 41, the gaseous sterilising agent may be introduced through the single port 41. In some embodiments, the flow of gaseous sterilising agent may be actively promoted, e.g. using a pressure gradient between the ports 41. In other embodiments, the gaseous sterilising agent may flow between the ports 41 passively, e.g. by diffusion.

The step S3 of introducing the gaseous sterilising agent then comprises flowing the gaseous sterilising agent through the tubing 51, with the tubing valve 53 open. The gaseous sterilising agent is thereby able to flow through the tubing 51 and tubing valve 53 into the cavity 45. This will sterilise the interior of the cavity 45, including the sensing elements 5 and other parts of the sensor component 1 that will be in contact with fluid in the fluid line 3 during use of the sensor component 1. The gaseous sterilising agent preferably remains in the cavity 45 for at least 1 hour, optionally 2 hours, optionally 4 hours, optionally 6 hours, before carrying out the step of replacing the gaseous sterilising agent. This ensures that the interior of the cavity 45 is fully sterilised.

The step S3 of introducing a gaseous sterilising agent into the cavity 45 as illustrated in FIG. 6 comprises placing the sensor component 1 into a sealed environment and introducing the gaseous sterilising agent into the sealed environment. The sealed environment may be, for example, a sterilisation bag or other container. This is a convenient way to ensure the sensor component 1 is totally exposed to the gaseous sterilising agent, and allows for the entire sensor component 1 to be sterilised, not only the cavity 45 interior. The gaseous sterilising agent may diffuse into the cavity 45 and interior spaces of the sensor component 1 via the ports 41, whether or not the tubing 51 and tubing valve 53 are present.

Figure 7:
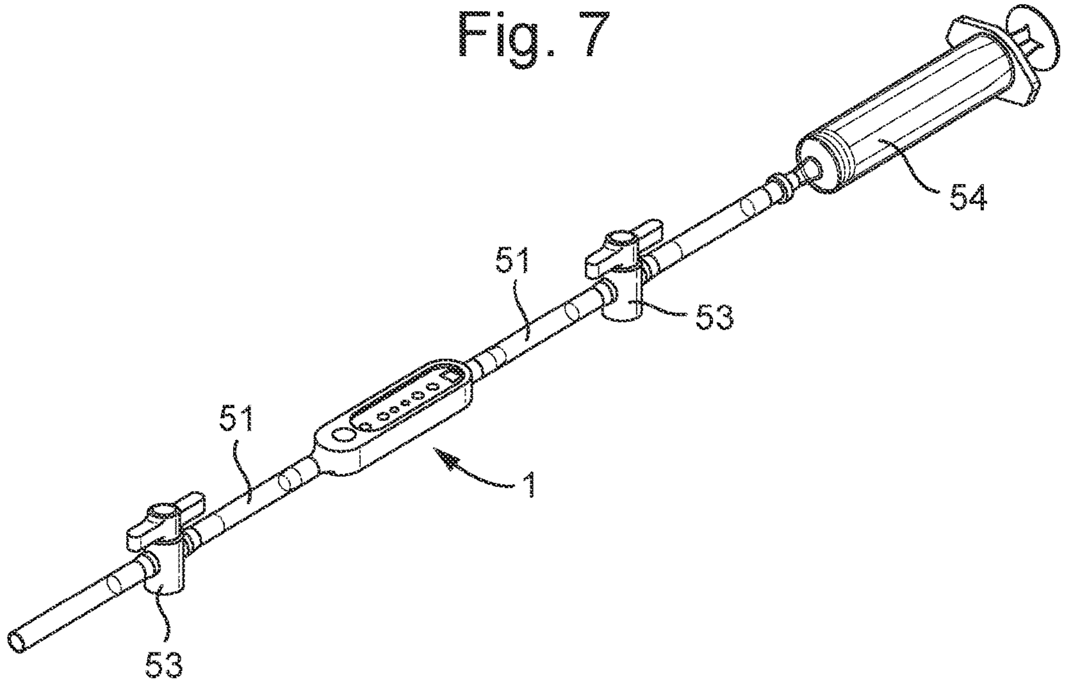
FIG. 7 shows a sensor component during replacement of the gaseous sterilising agent with a sterile liquid.

As illustrated in FIG. 7, following the step S3 of introducing a gaseous sterilising agent into the cavity 45, the method comprises replacing the gaseous sterilising agent with a sterile liquid via the ports 41. Similarly as for the step S3 of introducing the gaseous sterilising agent, replacing the gaseous sterilising agent comprises flowing the sterile liquid between the two ports, but may be correspondingly adapted where there is only one port 41. The sterile liquid is flowed through the tubing 51 with the tubing valve 53 open. The sterile liquid is preferably water-based, for example a buffer solution such as a phosphate buffer solution. Preferably, the sterile liquid is a calibration solution containing predetermined concentrations of the one or more analytes. This can aid in later calibration of the sensor component 1 at the point of use. In FIG. 7, the sterile liquid is contained in a syringe 54, and the syringe 54 is connected to the tubing 51 and used to flow the sterile liquid through the tubing 51 between the ports 41 and into the cavity 45. Following the step of replacing the gaseous sterilising agent with the sterile liquid, the cavity 45 remains filled with the sterile liquid, thereby ensuring that the sensing elements 5 remain in a hydrated state when the sensor component 1 is delivered to the end user.

Replacing the gaseous sterilising agent with a sterile liquid via the ports 41 comprises replacing the gaseous sterilising agent with a sterile gas via the ports 41, and subsequently introducing S9 the sterile liquid via the ports 41. When introducing S9 the sterile liquid, the sterile liquid will replace the sterile gas. This reduces the chance that any liquid will come into contact with the gaseous sterilising agent, which may be undesirable depending on the choice of gaseous sterilising agent. The use of the syringe 54 to introduce the sterile liquid in FIG. 7 is only performed once the gaseous sterilising agent has been replaced with the sterile gas. The sterile gas is preferably a relatively inert gas such as nitrogen or a noble gas to ensure no chemical interaction occurs with the sensor component 1. Alternatively, the sterile gas may be sterile air, which may be easier and cheaper to provide. The gaseous sterilising agent is removed and replaced by a sterile gas such as air before the sterile liquid is introduced, otherwise water in the sterile liquid could react with the gaseous sterilising agent. For example, ethylene oxide reacts with water to form ethylene glycol, which is toxic and difficult to remove from the sensor component 1 once formed. Where contact between the gaseous sterilising agent and water is not problematic, the step of replacing the gaseous sterilising agent with a sterile gas may be omitted, and replacing the gaseous sterilising agent with a sterile liquid may comprise directly displacing the gaseous sterilising agent with the sterile liquid.

Replacing the gaseous sterilising agent with a sterile gas via the ports 41 comprises removing S5 the gaseous sterilising agent by evacuation via the ports 41, and subsequently introducing S7 the sterile gas via the ports 41. This ventilation/aeration ensures that the gaseous sterilising agent is completely removed from the sensor component 1 and cavity 45. This may be necessary, for example because ethylene oxide and other gaseous sterilising agents are toxic, and it is a regulatory requirement that all the gaseous sterilising agent is removed as part of the sterilisation process to ensure that no residuals are left that could be harmful to a patient.

Where introducing S3 the gaseous sterilising agent into the cavity 45 comprises placing the sensor component 1 into a sealed environment, replacing the gaseous sterilising agent with the sterile liquid is carried out without removing the sensor component 1 from the sealed environment. The syringe 54 may be sterilised in the same sealed environment as the sensor component 1, tubing 51, and tubing valves 53 in order that no contamination is introduced when the syringe 54 is connected to the tubing 51.

Figure 8:
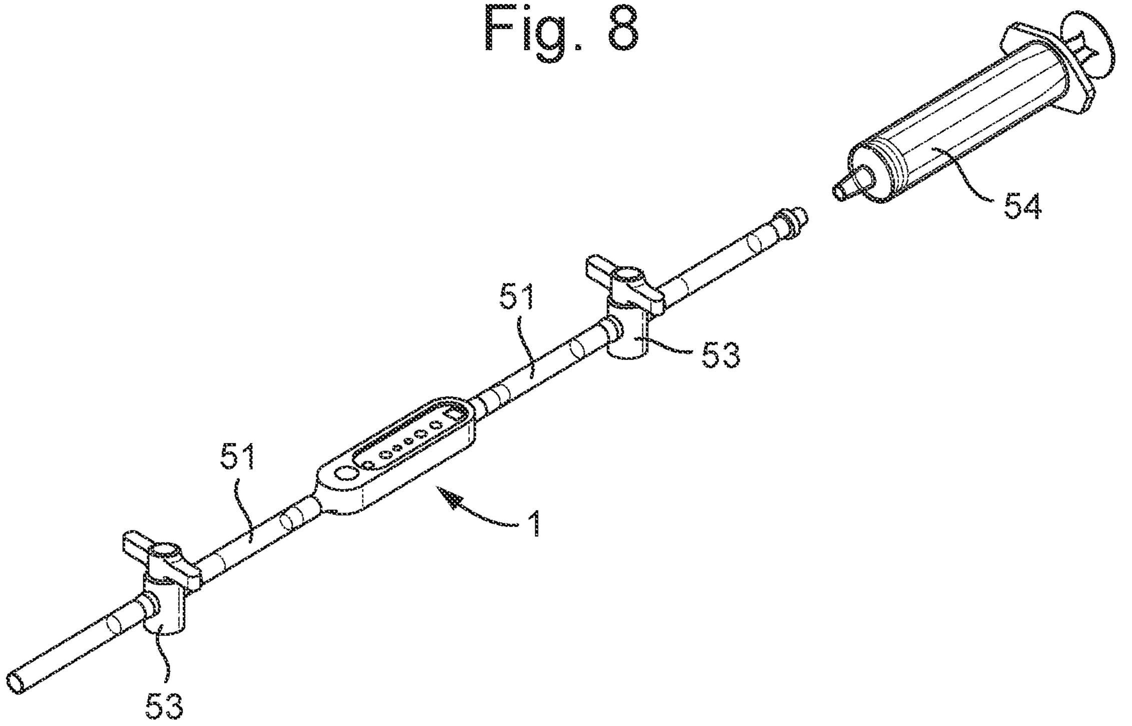
FIG. 8 shows a sensor component during sealing of the ports.

Following the replacement of the gaseous sterilising agent with a sterile liquid via the ports 41, the method comprises sealing the ports 41, as illustrated in FIG. 8. The sensor component 1 shown in FIGS. 1 to 3 and FIGS. 6 to 8 comprises dedicated ports 41 that are used for the sterilisation method, and are not subsequently needed during use of the sensor component 1. In such cases, the method may comprise permanently sealing the ports 41. Alternatively, sealing the ports 41 may comprise sealing the ports 41 with removable elements 43.

As illustrated in FIG. 8, the method comprises closing S11 the tubing valves 53 prior to the step of sealing the ports 41. This ensures that the sterile liquid remains in the cavity 45. Then the step of sealing the ports 41 comprises sealing S13 the tubing 51, and cutting S15 the tubing 51 outside the position where the tubing 51 is sealed such that a sealed section of the tubing 51 remains connected to the ports 41. Specifically, the tubing 51 is cut between the position where the tubing 51 is sealed and the tubing valve 53. With reference to FIG. 8, the tubing 51 may be sealed between the tubing valve 53 and the port 41. The sealed section of the tubing may function as the removable elements 43 sealing the ports 41, or may be permanently joined to the ports 41, in which case they would permanently seal the ports 41. The tubing 51 may be sealed using any suitable method, for example ultrasonic welding or solvent sealing.

Not all of the steps of the method may be performed in the same location. For example, the introduction S3 of a gaseous sterilising agent, and replacement of the gaseous sterilising agent with a sterile gas may be carried out in one location. The sterile sensor component 1 may then be transported to another location in a sterile container (for example a sterilisation bag that constitutes the sealed environment discussed above). The replacement of the sterile gas with the sterile liquid and sealing of the ports may then be carried out in the other location. This may be facilitated by sterilising the syringe 54 containing the sterile liquid together with the sensor component 1 in the sealed environment, as mentioned above. The replacement of the sterile gas with the sterile liquid and closing S11 of the tubing valves 53 can then be carried out without removing the sensor component 1 from the sealed environment.

Figure 9:
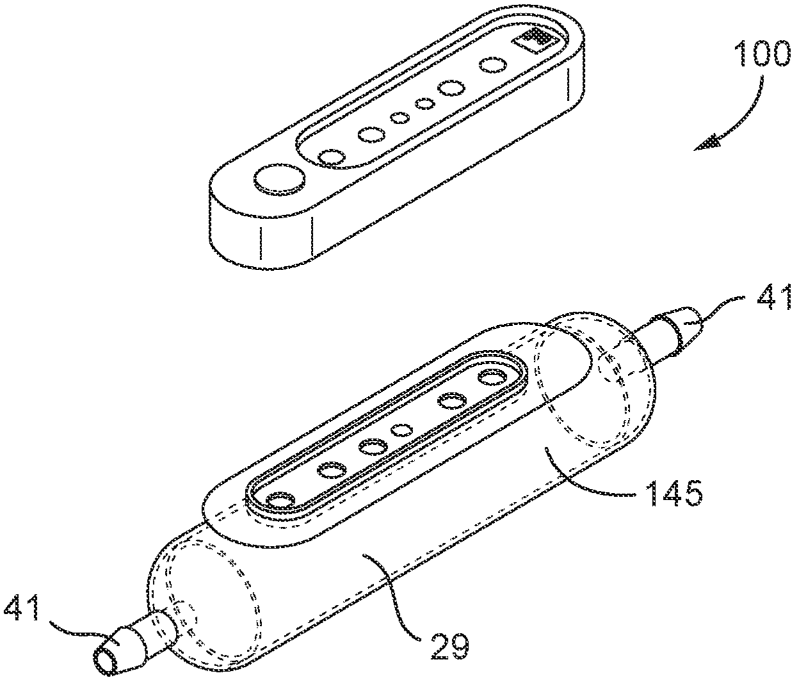
FIG. 9 is an exploded view of a sensor component comprising a conduit, showing how the conduit may be joined to the remainder of the sensor component.

The method has so far been discussed in the context of the sensor component 1 of FIGS. 1 to 3, which is configured to be engaged with a wall of the fluid line 3. In other cases, the method may be applied to a sensor component configured to engage with the fluid line 3 in an in-line configuration, or in a bypass (or shunt) configuration. An example of such a sensor component 100 is shown in FIG. 9. In this example, the sensor component 100 defines a cavity 145, but the cavity 145 is not defined between the sensor elements 5 and a removable seal 47. Rather, the cavity 145 is defined by a conduit 29 that is configured to be inserted into the fluid line 3 for engagement of the sensor component 100 with the fluid line 3. In this case, as well as the ports 41 that provide fluid connection to the cavity 145 being used during sterilisation, the ports 41 are further used to allow fluid from the fluid line 3 to come into contact with the sensing elements 5 during use.

In some embodiments, the conduit 29 is configured to be inserted into the fluid line 3 in an in-line configuration. In such cases, the conduit 29 becomes a part of the main fluid line 3. It may be preferable in such situations that the ports 41 are sealed using removable elements 43 as described above, so the ports 41 can be unsealed immediately prior to inserting the conduit 29 into the fluid line 3.

Figure 10:
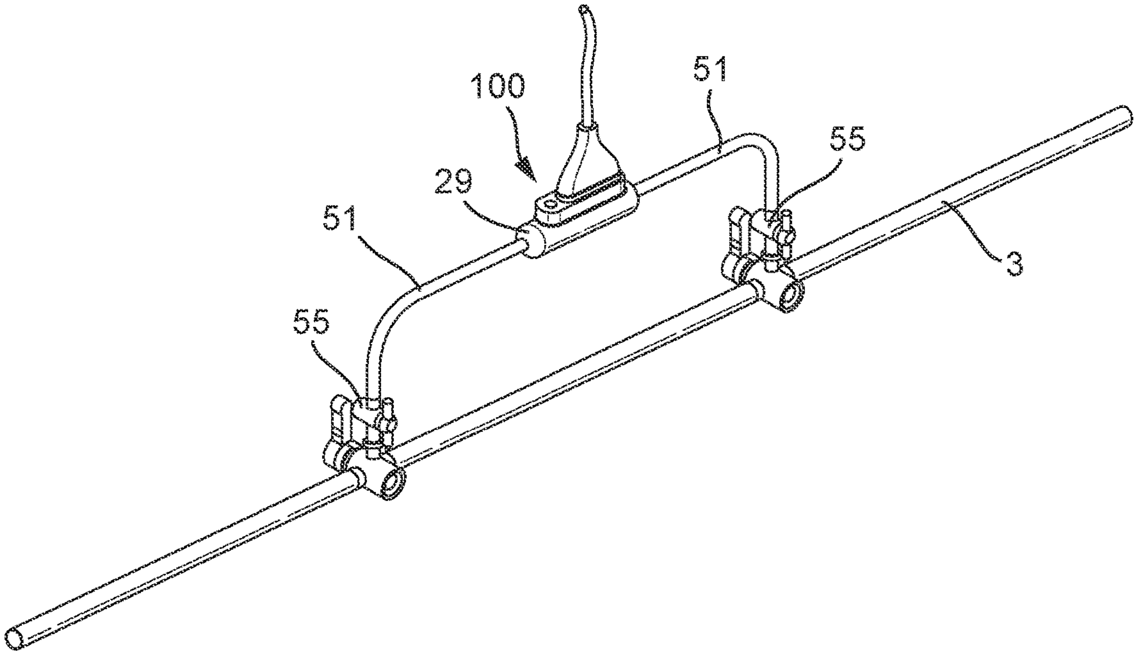
FIG. 10 shows a sensor component comprising a conduit engaged with the fluid line in a bypass configuration.

FIG. 10 shows another embodiment in which the conduit 29 is configured to be inserted into the fluid line 3 in a shunt configuration. This may be preferable in some situations because it allows the sensor component to be connected and disconnected from the fluid line 3 without having to interrupt the flow of fluid in the fluid line 3.

Figure 11:
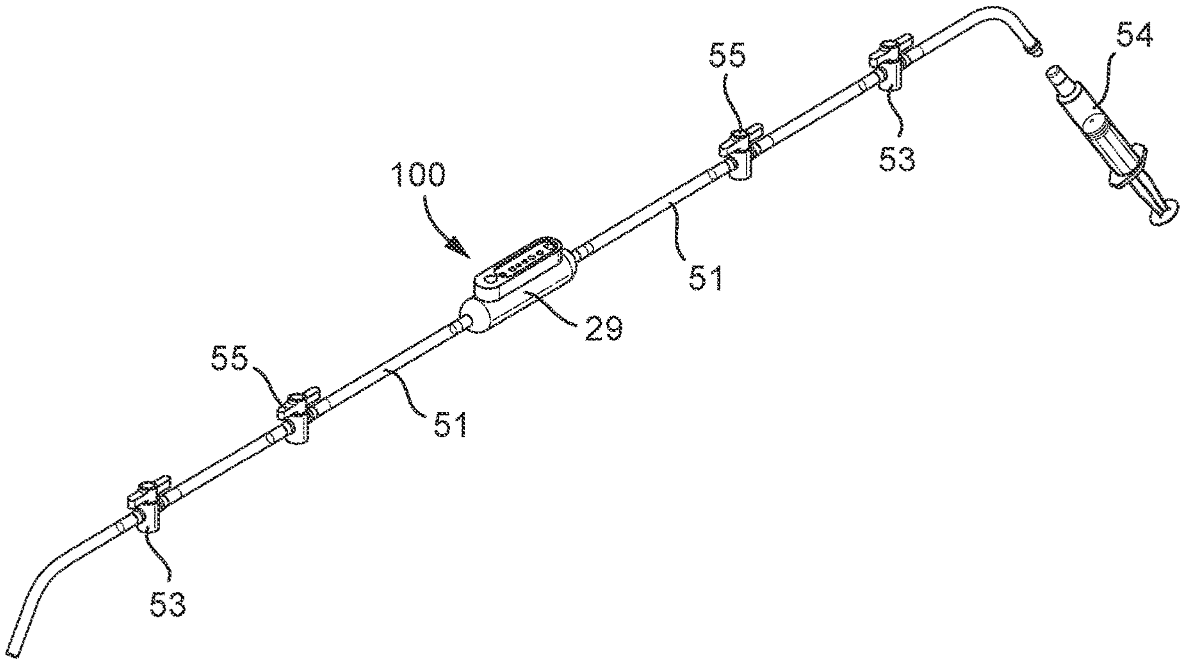
FIG. 11 shows a sensor component comprising a conduit and component valves during introduction of the gaseous sterilising agent.
Figure 12:
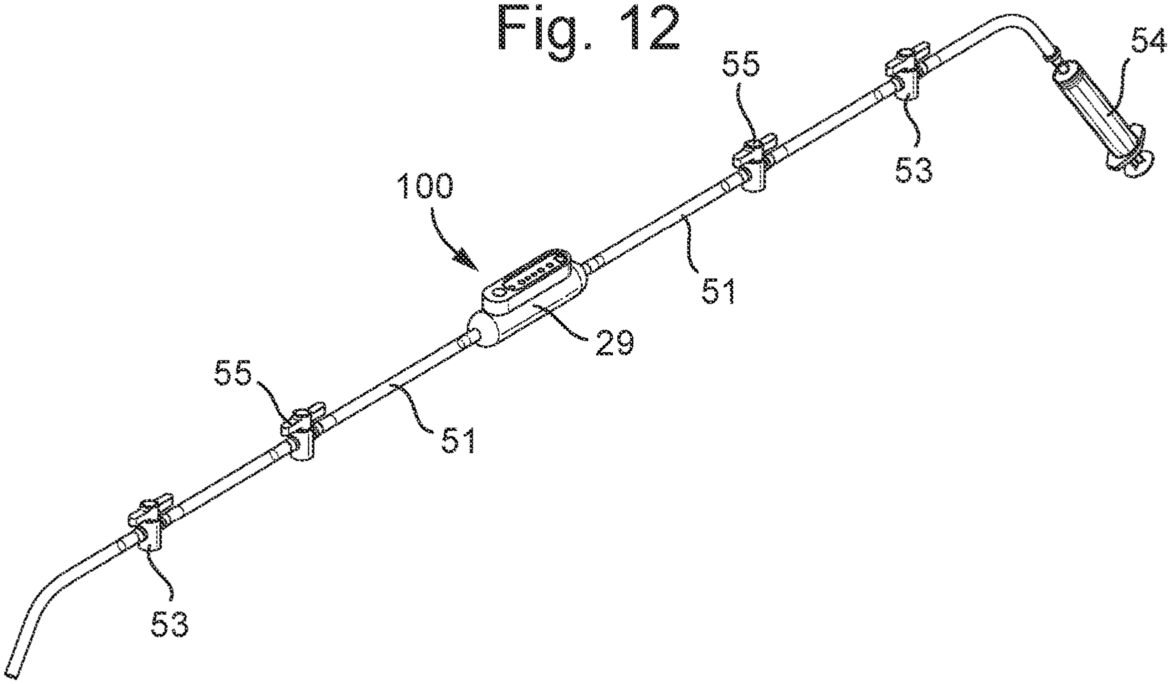
FIG. 12 shows a sensor component comprising a conduit and component valves during replacement of the gaseous sterilising agent with a sterile liquid.
Figure 13:
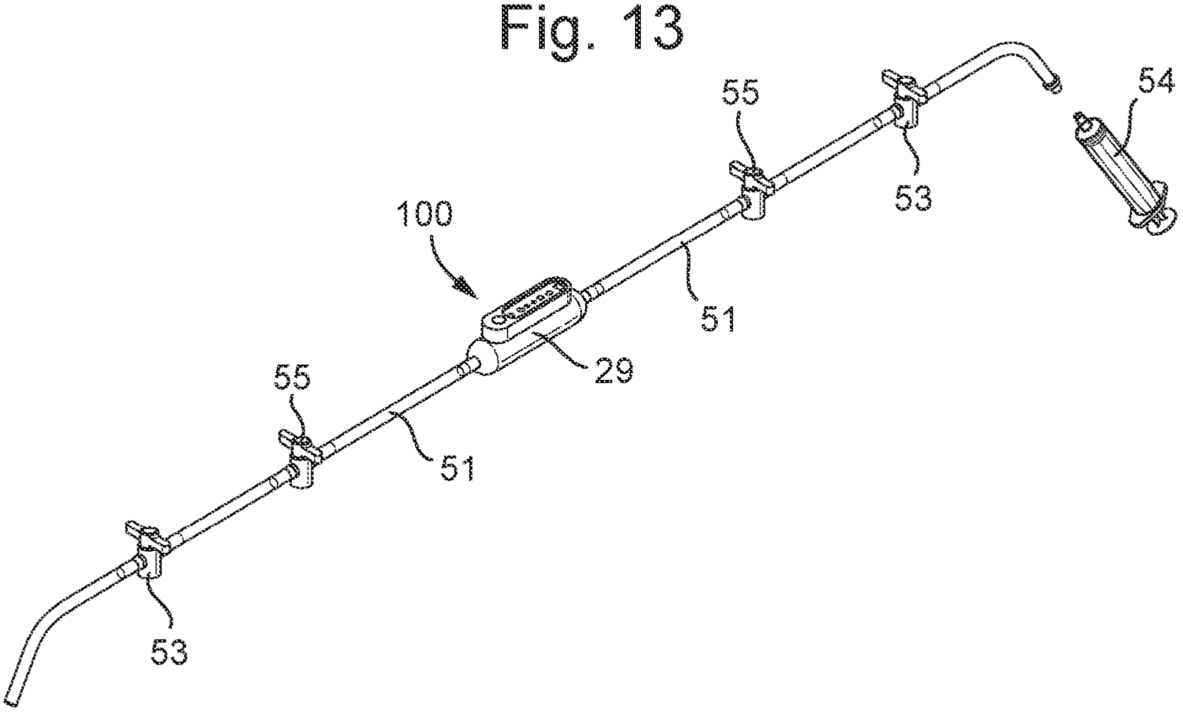
FIG. 13 shows a sensor component comprising a conduit and component valves during sealing of the ports.

FIGS. 11-13 show an embodiment of the method applied to a sensor component 100 with a cavity 145 defined by the conduit 29. The sensor component 100 further comprises a component valve 55 in respect of each port 41, configured to open and close the port 41. Component valves 55 may be preferred, particularly where the sensor component 100 is configured to be inserted into the fluid line 3 in a shunt configuration, but are not in general essential. The steps of the method are largely unchanged from those described in relation to the sensor component 1 of FIGS. 1 to 3, except as identified below.

The step S1 of preconditioning the sensor component 100 is as described above for the sensor component 100.

FIG. 11 shows the step S3 of introducing the gaseous sterilising agent. In FIG. 11, tubing 51 and tubing valves 53 are present although this is not in general essential. The sensor component 100 comprises component valves 55 connected to the ports 41, and connecting the tubing 51 to the ports 41 comprises connecting the tubing to the component valves 55. Introducing S3 the gaseous sterilising agent is as described above, but additionally with the component valve 55 open. As described above, the step is performed with the tubing valves 53 open.

FIG. 12 shows the step of replacing the gaseous sterilising agent with a sterile liquid. Similarly to the step S3 of introducing the gaseous sterilising agent, this step is as described for the sensor component 1 above, but with the component valves 55 open.

Figure 14:
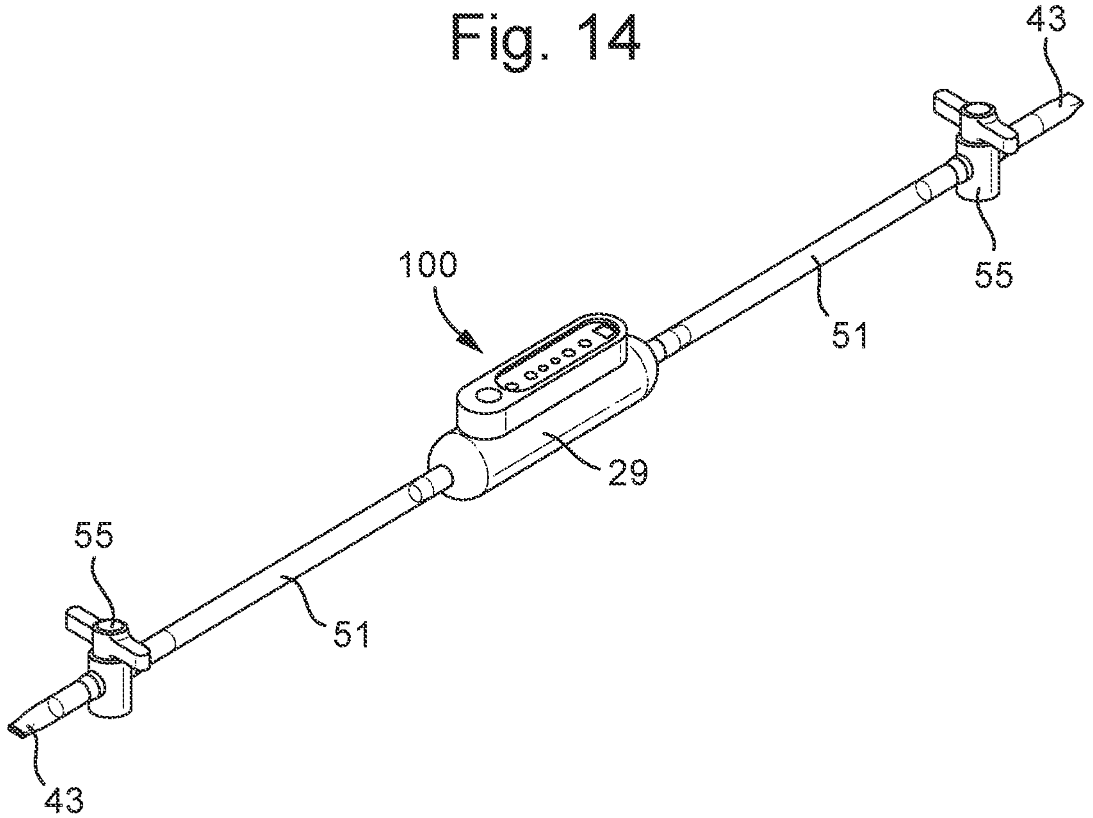
FIG. 14 shows a sensor component comprising a conduit and component valves after the sterilisation method is complete.

FIG. 13 shows the step of sealing the one or more ports 41. This is as described above for the sensor component 1, but the step S11 of closing the valves also comprises closing the component valve 55. The step S13 of sealing the tubing is performed at least in part by the closing of the component valve 55, which seals the tubing 51. For the sensor component 100, the step S15 comprises cutting the tubing 51 outside of the position where the tubing 51 is sealed by the component valve 55 such that the component valve 55 remains connected to the ports 41. The tubing 51 may additionally be sealed in step S13 outside of the component valve 55, for example between the component valve 55 and tubing valve 53 by one of the methods mentioned above, and cut in step S15 such that a sealed section 43 of the tubing 51 remains connected to the component valve 55, as illustrated in FIG. 14. This sealed section of tubing 51 thereby provides a removable element 43.

The method may also be applied to other types of sensor component, including a sensor component which does not itself define a cavity and does not comprise the ports 41. In all of the embodiments discussed so far, a cavity is defined by the sensor component, for example via a removable seal 47 or by the conduit 29. However, this is in general not necessary for the sterilisation method discussed herein to be applicable.

Figure 15:
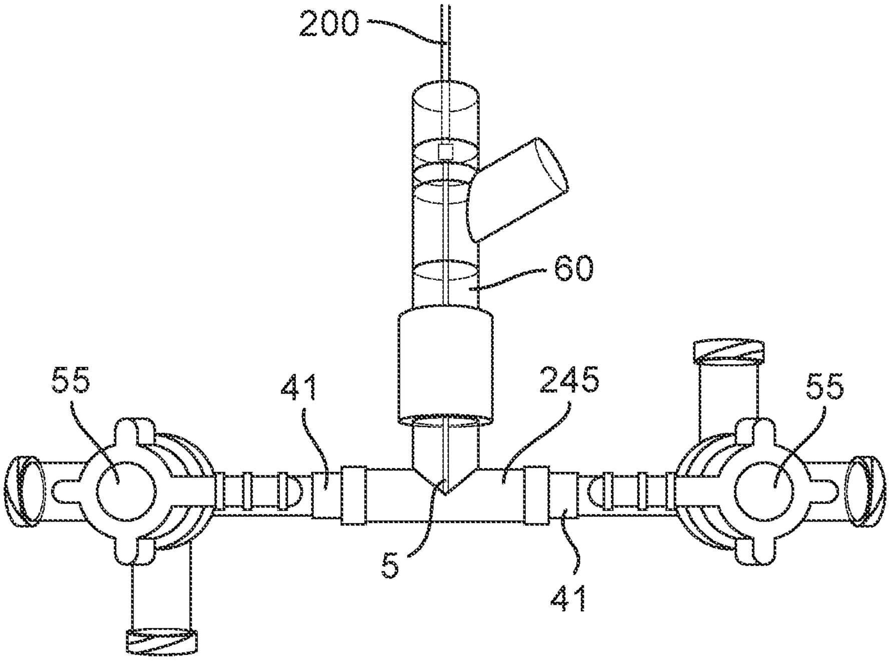
FIG. 15 shows an intravascular sensor component where the sensor component does not comprise the cavity to which the sensing elements are exposed during sterilisation.

FIG. 15 shows an intravascular sensor component 200, which comprises an optical waveguide with a sensing element 5 placed at the end of the waveguide. The intravascular sensor component 200 may be configured to engage with a fluid line such as a blood vessel inside a patient's body. The intravascular sensor component 200 does not define a cavity. Instead, a container 60 defines a cavity 245, and the container further comprises the ports 41. In FIG. 15, the container 60 also comprises component valves 55, but this is not in general essential. The method described above is still applicable to this type of intravascular sensor component 200.

The step S1 of preconditioning the sensor component 200 is still performed as described above.

Prior to the step S3 of introducing the gaseous sterilising agent, the intravascular sensor component 200 is removably inserted into the cavity 245. The container 60 is configured such that the sensor component 200 forms a seal with the container when it is inserted into the cavity 245. This prevents fluid (for example, the gaseous sterilising agent, sterile gas, or sterile liquid) flowing in or out of the cavity 245 except via the ports 41 during the sterilisation method. It also ensures that the sterile liquid will remain in contact with the sensing element 5 after the completion of the sterilisation method so that the intravascular sensor component 200 is delivered to the end user in a hydrated state.

Tubing 51 and tubing valves 53 may be connected to the component valves 55 as described for the sensor component 100 in FIG. 11 above. The step S3 of introducing the gaseous sterilising agent would be performed with the component valves 55 of the container 60 open.

The steps of replacing the gaseous sterilising agent with a sterile liquid, and sealing the one or more ports 41 would also be performed as described for the sensor component 100 above. In the case of the sensor component 200 of FIG. 15, no sections of tubing 51 are left attached to the component valves 55. Embodiments similar to this can be applied to other types of sensor component that do not define a cavity, and not only to intravascular sensor components 200.

The invention claimed is:

1. A method of sterilising a sensor component for use in a system for measuring the concentration of one or more analytes in fluid in a fluid line, the method comprising:

providing a sensor component comprising one or more ports providing fluid connection to a cavity and configured to expose one or more sensing elements in a dry state to the fluid in the fluid line, the one or more sensing elements having an optical property that varies with the concentration of the one or more analytes in the fluid; and a connector configured to connect to one or more optical waveguides, the sensor component being configured to transmit light between the one or more optical waveguides and the one or more sensing elements;

the method further comprising:

connecting tubing to the one or more ports;

introducing a gaseous sterilising agent into the cavity via the one or more ports providing fluid connection to the cavity, wherein: i) the one or more sensing elements are exposed to the cavity and are thereby sterilised by the gaseous sterilising agent, and ii) introducing the gaseous sterilising agent comprises flowing the gaseous sterilising agent through the tubing;

hydrating the one or more sensing elements by replacing the gaseous sterilising agent with a sterile liquid via the one or more ports, wherein replacing the gaseous sterilising agent with the sterile liquid comprises flowing the sterile liquid through the tubing; and sealing the one or more ports, wherein sealing the one or more ports comprises sealing the tubing, and cutting the tubing outside the position where the tubing is sealed such that a sealed section of the tubing remains connected to the one or more ports.

2. A method according to claim 1, wherein the step of introducing a gaseous sterilising agent into the cavity comprises placing the sensor component into a sealed environment and introducing the gaseous sterilising agent into the sealed environment, the step of replacing the gaseous sterilising agent being carried out without removing the sensor component from the sealed environment.

3. A method according to claim 1, wherein the gaseous sterilising agent remains in the cavity for at least 1 hour before carrying out the step of replacing the gaseous sterilising agent.

4. A method according to claim 1, further comprising preconditioning the sensor component prior to introducing the gaseous sterilising agent by exposing the sensor component to a predetermined temperature for a predetermined length of time.

5. A method according to claim 1, wherein replacing the gaseous sterilising agent with a sterile liquid via the one or more ports comprises replacing the gaseous sterilising agent with a sterile gas via the one or more ports, and subsequently introducing the sterile liquid via the one or more ports.

6. A method according to claim 5, wherein replacing the gaseous sterilising agent with a sterile gas via the one or more ports comprises removing the gaseous sterilising agent by evacuation via the one or more ports, and subsequently introducing the sterile gas via the one or more ports.

7. A method according to claim 1, wherein the method is carried out at a temperature in a range from 35° C. to 65° C.

8. A method according to claim 1, wherein the gaseous sterilising agent is one of ethylene oxide, ozone, hydrogen peroxide, nitrogen dioxide, and formaldehyde.

9. A method according to claim 1, wherein the sterile liquid is a calibration solution containing predetermined concentrations of the one or more analytes.

10. A method according to claim 1, wherein the one or more ports comprise two ports, and the steps of introducing the gaseous sterilising agent and replacing the gaseous sterilising agent comprise flowing the gaseous sterilising agent and sterile liquid between the two ports.

11. A method according to claim 1, wherein sealing the one or more ports comprises permanently sealing the one or more ports.

12. A method according to claim 1, wherein sealing the one or more ports comprises sealing the one or more ports with removable elements.

13. A method according to claim 1, wherein:

the tubing comprises a tubing valve configured to open and close the tubing, the step of introducing the gaseous sterilising agent is performed with the tubing valve open;

the step of replacing the gaseous sterilising agent is performed with the tubing valve open;

the tubing is cut between the position where the tubing is sealed and the tubing valve; and the method further comprises closing the tubing valve prior to the step of sealing the one or more ports.

14. A method according to claim 1, wherein the tubing is sealed using ultrasonic welding or solvent sealing.

15. A method according to claim 1, wherein the sensor component further comprises one or more component valves, wherein each of the one or more component valves is fluidly connected to and configured to open and close a respective port of the one or more ports;

the step of introducing the gaseous sterilising agent is performed with the one or more component valves open;

the step of replacing the gaseous sterilising agent is performed with the one or more component valves open; and the step of sealing the one or more ports comprises closing the one or more component valves.

16. A method according to claim 1, wherein the sensor component defines the cavity and comprises the one or more ports.

17. A method according to claim 16, wherein the sensor component is configured to engage with a wall of the fluid line.

18. A method according to claim 17, wherein the sensing elements are covered by a removable seal, the cavity being defined between the sensing elements and the removable seal.

19. A method according to claim 16, wherein the cavity is a conduit that is configured to be inserted into the fluid line for engagement of the sensor component with the fluid line.

20. A method according to claim 19, wherein the conduit is configured to be inserted into the fluid line in an in-line configuration.

21. A method according to claim 19, wherein the conduit is configured to be inserted into the fluid line in a shunt configuration.

22. A method according to claim 1, wherein a container defines a container cavity and the sensor component is removably inserted into the container cavity prior to introducing the gaseous sterilising agent.

* * * * *